US010602998B2

(12) United States Patent
Smith et al.

(10) Patent No.: US 10,602,998 B2
(45) Date of Patent: Mar. 31, 2020

(54) METHODS AND SYSTEMS FOR DYNAMICALLY MODIFYING ACQUISITION PARAMETER DURING IMAGE ACQUISITION

(71) Applicant: HOLOGIC, INC., Marlborough, MA (US)

(72) Inventors: Andrew P. Smith, Lexington, MA (US); Julian Marshall, Los Altos, CA (US)

(73) Assignee: Hologic, Inc., Marlborough, MA (US)

( * ) Notice: Subject to any disclaimer, the term of this patent is extended or adjusted under 35 U.S.C. 154(b) by 240 days.

(21) Appl. No.: 15/357,326

(22) Filed: Nov. 21, 2016

(65) Prior Publication Data
US 2017/0065238 A1    Mar. 9, 2017

Related U.S. Application Data

(63) Continuation of application No. 14/986,489, filed on Dec. 31, 2015, now Pat. No. 9,498,176, which is a
(Continued)

(51) Int. Cl.
*A61B 6/00* (2006.01)
*A61B 34/30* (2016.01)
(Continued)

(52) U.S. Cl.
CPC ............ *A61B 6/4417* (2013.01); *A61B 5/055* (2013.01); *A61B 6/025* (2013.01); *A61B 6/037* (2013.01);
(Continued)

(58) Field of Classification Search
CPC ....... A61B 6/4417; A61B 34/30; A61B 5/055; A61B 6/025; A61B 6/037; A61B 6/461;
(Continued)

(56) References Cited

U.S. PATENT DOCUMENTS 5,657,362 A    8/1997    Giger et al.
6,990,171 B2   1/2006    Toth et al.
(Continued)

FOREIGN PATENT DOCUMENTS

DE    10353611    6/2005
WO    WO 2006058160    6/2006
(Continued)

OTHER PUBLICATIONS

Extended European Search Report for EP Application No. 11180742, dated Jan. 1, 2016 (6 pages).
(Continued)

*Primary Examiner* — Courtney D Thomas
(74) *Attorney, Agent, or Firm* — Vista IP Law Group, LLP

(57) ABSTRACT

Systems and methods for automatically and dynamically modifying an image acquisition parameter for use in tomosynthesis breast imaging. A selected image acquisition parameter is modified in response to a measured characteristic of an imaged object such as a breast, and thus tailored to provide the highest quality image for the particular object. For example, image quality in a breast tomosynthesis system can be improved by dynamically varying motion and other acquisition parameters of the tomosynthesis system in response to physical characteristics of the breast to be imaged (determined during image acquisition), such as the breast thickness, density or composition. Dynamically varying acquisition or processing methods helps to customize the system for each particular patient, thereby improving image quality and identification and assessment of potential pathologies and abnormalities, and lower radiation dose, and thus a reduced risk of long-term adverse health effects due to lifetime accumulated radiation dose.

36 Claims, 4 Drawing Sheets

Related U.S. Application Data continuation of application No. 14/600,457, filed on Jan. 20, 2015, now Pat. No. 9,241,681, which is a continuation of application No. 14/287,600, filed on May 27, 2014, now Pat. No. 8,942,443, which is a continuation of application No. 13/229,052, filed on Sep. 9, 2011, now Pat. No. 8,744,041.

(60) Provisional application No. 61/381,438, filed on Sep. 9, 2010.

(51) Int. Cl.
| | |
|---|---|
| *A61B 6/02* | (2006.01) |
| *A61B 8/14* | (2006.01) |
| *A61B 5/055* | (2006.01) |
| *A61B 6/03* | (2006.01) |
| *A61B 8/08* | (2006.01) |

(52) U.S. Cl.
CPC ............ *A61B 6/461* (2013.01); *A61B 6/467* (2013.01); *A61B 6/488* (2013.01); *A61B 6/502* (2013.01); *A61B 6/5211* (2013.01); *A61B 6/5217* (2013.01); *A61B 6/54* (2013.01); *A61B 6/544* (2013.01); *A61B 6/545* (2013.01); *A61B 8/0825* (2013.01); *A61B 8/14* (2013.01); *A61B 8/483* (2013.01); *A61B 34/30* (2016.02)

(58) Field of Classification Search
CPC ......... A61B 6/467; A61B 6/488; A61B 6/502; A61B 6/5211; A61B 6/5217; A61B 6/54; A61B 6/544; A61B 6/545; A61B 8/0825; A61B 8/14; A61B 8/483
USPC .......................................................... 378/37
See application file for complete search history.

(56) References Cited

U.S. PATENT DOCUMENTS

| | | | |
|---|---|---|---|
| 7,123,684 | B2 | 10/2006 | Jing et al. |
| 7,245,694 | B2 | 7/2007 | Jing et al. |
| 7,443,949 | B2 | 10/2008 | Defreitas et al. |
| 7,542,792 | B2 | 6/2009 | Wollenweber et al. |
| 8,744,041 | B2 | 6/2014 | Smith et al. |
| 8,942,343 | B2 | 1/2015 | Smith et al. |
| 9,241,681 | B2 | 1/2016 | Smith et al. |
| 2004/0202279 | A1 | 10/2004 | Besson et al. |
| 2007/0274585 | A1 | 11/2007 | Zhang et al. |
| 2008/0056441 | A1 | 3/2008 | Souchay et al. |
| 2008/0075225 | A1 | 3/2008 | Kalender |
| 2008/0112534 | A1 | 5/2008 | Defreitas et al. |
| 2009/0003679 | A1 | 1/2009 | Ni et al. |
| 2009/0022273 | A1 | 1/2009 | Kashiwagi et al. |
| 2009/0323892 | A1 | 12/2009 | Hitzke et al. |
| 2010/0111379 | A1 | 5/2010 | Suri et al. |
| 2010/0226475 | A1 | 9/2010 | Smith et al. |
| 2014/0133626 | A1 | 5/2014 | Jang et al. |

FOREIGN PATENT DOCUMENTS

| | | |
|---|---|---|
| WO | 2007/056574 | 5/2007 |
| WO | 2010/028208 | 3/2010 |

OTHER PUBLICATIONS

Search Report for German Patent Application File No. 20 2009 018 884.1, Applicant Hologic, Inc., dated Mar. 17, 2014, 5 pages, in German language, no translation received.

Highnam, Brady, and Shepstone, "Mammographic Image Analysis", Eur. J. Radiology, Jan. 1997; 24(1)20-32 (13 pages).

"Understanding R2 Quantra 1.3," PN MAN-01224 Rev 001, Hologic, Inc., issued Apr. 2009 (22 pages).

Kontos, et al., "A Comparative Study of Volumetirc and Area-Based Breast Density Estimation in Digital Mammography: Results from a Screening Population," Digital Mammography IWDM 2010: 378-385 (2010) (8 pages).

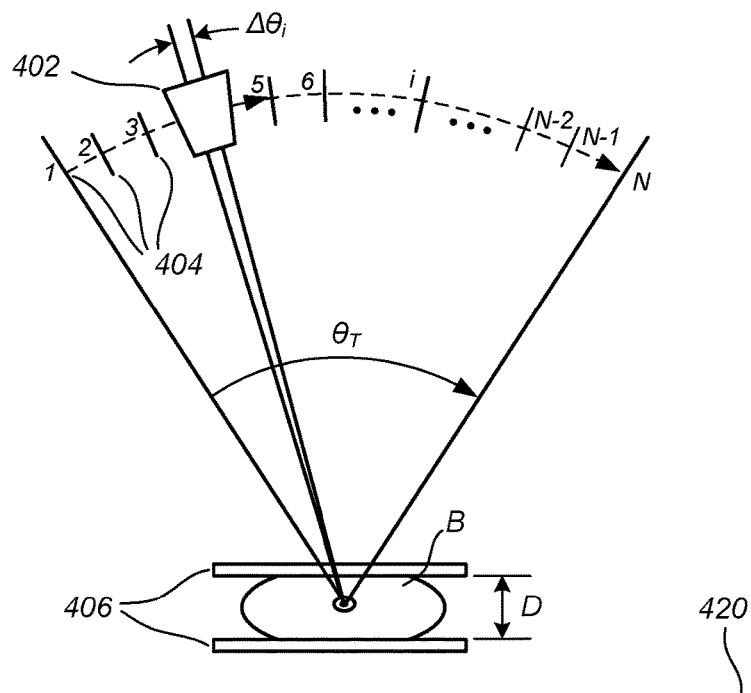

| TOMOSYNTHESIS IMAGING ARC | $\theta_T$ | |
| --- | --- | --- |
| NUMBER OF PROJECTION IMAGES | $N$ | |
| OVERALL GANTRY SWEEP TIME | $T$ | |
| ANGULAR VELOCITY | $\omega$ | $\theta_T = \omega T$ |
| EXPOSURE WINDOW | $\Delta t_i$ | |
| BLUR ANGLE | $\Delta \theta_i$ | $\Delta \theta_i = (\Delta t_i)(\omega)$ |
| TUBE CURRENT | $mA$ | |
| MILLIAMP SECONDS PER PROJECTION | $mAs_i$ | $mAs_i = (mA)(\Delta t_i)$ |
| MILLIAMP SECONDS TOTAL | $mAs_T$ | $mAs_T = N(mAs_i) = N(mA)(\Delta t_i)$ |

FIG. 4

METHODS AND SYSTEMS FOR DYNAMICALLY MODIFYING ACQUISITION PARAMETER DURING IMAGE ACQUISITION

CROSS-REFERENCE TO RELATED APPLICATION

This application is a continuation of U.S. patent application Ser. No. 14/986,489, filed Dec. 31, 2015, now issued as U.S. Pat. No. 9,498,176, which is a continuation of U.S. patent application Ser. No. 14/600,457, filed Jan. 20, 2015, issued as U.S. Pat. No. 9,241,681, which is a continuation of U.S. patent application Ser. No. 14/287,600, filed May 27, 2014, issued as U.S. Pat. No. 8,942,343, which is a continuation of U.S. patent application Ser. No. 13/229,052, filed Sep. 9, 2011, issued as U.S. Pat. No. 8,744,041, which claims priority under 35 U.S.C. § 119 from provisional U.S. Patent Application Ser. No. 61/381,438, filed Sep. 9, 2010, the contents of which are incorporated herein by reference as though set forth in full.

FIELD OF THE INVENTION

Embodiments of the invention relate to medical imaging, and more particularly, to acquisition and analysis of medical images.

BACKGROUND

Millions of people have suffered from breast cancer and other types of cancer. It is estimated that in the United States, breast cancer mortality is second only to that of lung cancer. Because of its role in early tumor detection, mammography has become the most commonly used tool for breast cancer screening, diagnosis and evaluation in the United States. A mammogram is an x-ray image of inner breast tissue that is used to visualize normal and abnormal structures within the breasts. A common purpose of breast imaging is to identify and assess potential pathologies or other abnormalities, which most frequently appear as likely micro-calcifications, tumor masses and architectural distortions. Mammograms provide early cancer detection because they can often show breast lumps and/or calcifications before they are manually palpable.

While screening mammography is recognized as the most effective method for early detection of breast cancer, the modality has limitations. One problem with known mammogram systems and methods lies in their low specificity. More particularly, it is often difficult to determine whether a detected abnormality is associated with a cancerous or benign lesion. This difficulty arises from the fact that a mammogram is two dimensional (2D) representations of a three dimensional (3D) structure, and overlapping structures in the compressed breast may confound diagnosis. These difficulties are further complicated in view of different breast compositions.

For example, breast composition, including breast x-ray density and texture, can vary from one patient to another, from one breast to another of the same patient and even within a single breast. Some breasts are composed mainly of fatty tissue and are known as "fatty breasts," while others have a high percentage of fibro glandular tissue and are known as "dense breasts." Most breast compositions are somewhere in between.

Efforts to improve the sensitivity and specificity of breast x-rays have included the development of breast tomosynthesis systems. Breast tomosynthesis is a 3D imaging technology that involves acquiring images of a stationary compressed breast at multiple angles during a short scan. The individual images are then reconstructed into a series of thin, high-resolution slices that can be displayed individually or in a dynamic ciné mode. Reconstructed tomosynthesis slices reduce or eliminate the problems caused by tissue overlap and structure noise in single slice 2D mammography imaging. Digital breast tomosynthesis also offers the possibility of reduced breast compression, improved diagnostic and screening accuracy, fewer recalls, and 3D lesion localization. Examples of breast tomosynthesis systems are described in U.S. Pat. Nos. 7,245,694 and 7,123,684, commonly owned by the Assignee of this application, the contents of which are incorporated herein by reference.

One goal of any x-ray imaging system is to obtain the highest quality image while minimizing the patient dose. Tomosynthesis acquisition systems balance the two goals by identifying a scanning protocol that obtains sufficient data to generate a quality reconstruction. The scanning protocol defines the number of images obtain during a scan, the angular range of the scan and the duration of the exposures. For example, a current tomosynthesis product is designed to perform a sweep angle of 15 degrees in about 5 seconds, during which 15 projections are acquired. The scanning protocol is generally fixed and used on all breast sizes and compositions.

While certain 2-D mammography systems have been introduced that vary, for example, the exposure time based on a measured thickness of the breast (determined by a distance between compression paddles), in general breast imaging systems lack the capability of customizing image acquisition parameters according to one or more of the preferred embodiments described herein.

SUMMARY

Embodiments are generally directed to obtaining the highest quality images can be obtained by tailoring the operating parameters of the image acquisition device used to acquire the image according to the particular composition of the individual breast. For example, according to embodiments, it is realized that tomosynthesis image quality may be improved by dynamically varying image acquisition parameters based on the physical characteristics of the imaged object. According to one embodiment, in a breast x-ray tomosynthesis imaging system, prior to acquiring a plurality of tomosynthesis projection images at a respective plurality of gantry angles encompassing a tomosynthesis imaging arc, an initial or scout image of the breast is acquired by the tomosynthesis imaging system, the scout image comprising a 2D projection image acquired at a gantry angle, the scout image being acquired such that a generally low dose of x-ray radiation is applied, e.g., comparable to or less than the radiation dose associated with one of the tomosynthesis projection images. The scout image is then automatically processed to compute one or more measured characteristics of the breast, and the one or more measured characteristics are used to automatically determine a set of tomosynthesis image acquisition parameters, or operating parameters, that are tailored for that breast.

For example, one embodiment is directed to a method for acquiring a plurality of images of breast tissue during a scan of the breast tissue by an image acquisition device and comprises acquiring a first image of the breast tissue using the image acquisition device and processing the first image to determine a physical characteristic of the breast tissue.

The method further comprises deriving or modifying at least one operating parameter of the image acquisition device based at least in part upon the physical characteristic. The modified operating parameter(s) include a motion parameter of the image acquisition device. The method further comprises acquiring a plurality of projection images of the breast tissue using the image acquisition device and the at least one motion parameter. Further, according to another embodiment, a comparison involves a view from a present study with a view from a prior study, and in such embodiments in which the comparison is temporal, then the current value may be larger than the prior. In such cases, the positioning may be better that that of the prior such that more tissue is pulled into view onto a detector. However, if the value for the current is smaller than that of the prior, then the positioning may be worse such that less tissue is pulled onto the detector.

Another embodiment is directed to a computer-implemented method for acquiring a plurality of images of breast tissue during a scan of the breast tissue and that is performed or executed by an image acquisition device or system (or by one or more controllers, processors or other computer components thereof). The computer-implemented method comprises the image acquisition device acquiring a first image of the breast tissue, processing or analyzing first image data to determine or assess a selected or pre-determined physical characteristic of the breast tissue, and deriving or modifying at least one operating parameter that was previously utilized during acquisition of the first image based at least in part upon the physical characteristic. The modified operating parameter(s) include at least one modified motion parameter of the image acquisition device. The method further comprises acquiring a plurality of projection images of the breast tissue using the at least one motion parameter.

Yet another embodiment is directed to utilizing a 2D projection image to determine whether to proceed with additional 3D projection images. In one embodiment, a computer-implemented method for acquiring a plurality of images of breast tissue during a scan of the breast tissue by an image acquisition device comprises an image acquisition device (or controller, processor or computer thereof) acquiring a 2D projection image of the breast tissue, processing the 2D projection image to determine a physical characteristic of the breast tissue, determining whether a plurality of 3D projection images of the breast issue should be acquired based at least in part upon the physical characteristic, and acquiring the plurality of 3D projection images if it is determined that the physical characteristic satisfies pre-determined criteria such as a threshold value.

A further embodiment is directed to a computer-implemented method for acquiring a plurality of images of breast tissue during a scan of the breast tissue by an image acquisition device and comprises utilizing a 3D projection image to determine whether to proceed with additional 2D projection images. In one embodiment, a computer-implemented method for acquiring a plurality of images of breast tissue during a scan of the breast tissue by an image acquisition device comprises an image acquisition device (or controller, processor or computer thereof) acquiring a 3D projection image of the breast tissue, processing the 3D projection image to determine a physical characteristic of the breast tissue, determining whether a plurality of 2D projection images of the breast issue should be acquired based at least in part upon the physical characteristic, and acquiring the plurality of 2D projection images if it is determined that the physical characteristic satisfies pre-determined criteria such as a threshold value.

Yet another embodiment is directed to a method for detecting a possible patient positioning error during x-ray breast image acquisition of the same breast.

One embodiment involves positioning, under the control of a technician or user of an image acquisition device, a breast of a patient into a first compressed imaging position according to a first view of the image acquisition device and acquiring a first mammographic image of the breast in the first compressed imaging position. The method further comprises positioning, under the control of the technician or user, the breast into a second compressed imaging position according to a second view of the image acquisition device and acquiring a second mammographic image of the breast in the second compressed imaging position. The method further comprises processing the first and second mammographic images to compute, for each of the mammographic images, at least one breast volume assessment metric and comparing the at least one breast volume assessment metric for the first mammographic image to the at least one breast volume assessment metric for the second mammographic image. If the breast volume assessment metrics differ by more than a threshold amount, then at least one user interface device associated with the image acquisition device is activated to alert the technician or user of a possible breast positioning error based at least in part upon the difference.

According to certain embodiments, methods for detecting a possible patient position error are computer-implemented, e.g., performed by an image acquisition device or controller, processor or computer thereof, such that the image acquisition device acquires a first mammographic image of a breast in a first compressed imaging position according to a first view, wherein the breast was positioned by a user of the image acquisition device into the first compressed imaging position according to the first view, and acquires a second mammographic image of the breast in a second compressed imaging position according to a second view, wherein the breast was positioned by the user into the second compressed imaging position according to the second view. The image acquisition device processes the first and second mammographic images to compute, for each of the first and second mammographic images, at least one breast volume assessment metric and compares the at least one breast volume assessment metric for the first mammographic image to the at least one breast volume assessment metric for the second mammographic image. If the breast volume assessment metrics differ by more than a threshold amount, the image acquisition device activates at least one user interface device associated with the image acquisition device that alerts the user of a possible breast positioning error based at least in part upon the difference.

Yet another embodiment is directed to a computer-implemented method for acquiring a plurality of images of breast tissue during a scan of the breast tissue by a computer-controlled image acquisition device and comprises acquiring a first image of the breast tissue using a first imaging modality and a first image acquisition device and processing the first image to determine a physical characteristic of the breast tissue. The method further comprises determining that a plurality of projection images should be acquired using one or both of a second imaging modality different than the first imaging modality and a second image acquisition device different than the first image acquisition device. The method further comprises notifying an operator of the first image acquisition device that a plurality of additional images should be acquired using at least one of the second imaging modality and the second image acquisition device. Thus, for example, the operator may be notified that the plurality of additional images should be acquired using the second imaging modality and the first image acquisition device or that the plurality of additional images should be acquired using the second imaging modality and the second image acquisition device.

A further embodiment is directed to a method for detecting a possible patient positioning error during x-ray breast image acquisition of different patient breasts, which may involve the same or different views of different breasts.

One embodiment involves positioning, under the control of user of an image acquisition device, a first breast of a patient into a first compressed imaging position according to a first view of the image acquisition device, acquiring a first mammographic image of the first breast in the first compressed imaging position, positioning, under the control of the user, a second breast of the patient into a second compressed imaging position according to a second view of the image acquisition device, the second breast being opposite the first breast, and acquiring a second mammographic image of the second breast in the second compressed imaging position. The method further comprises processing the first and second mammographic images to compute, for each of the first and second mammographic images, at least one breast volume assessment metric and comparing the at least one breast volume assessment metric for the first mammographic image to the at least one breast volume assessment metric for the second mammographic image. If the breast volume assessment metrics differ by more than a threshold amount, activating at least one user interface device associated with the image acquisition device that alerts the user of a possible breast positioning error based at least in part upon the difference.

Another embodiment is directed to a computer-implemented method for detecting a possible patient positioning error during x-ray breast image acquisition, the method comprising and involves an image acquisition device (or controller, processor or computer thereof) acquiring a first mammographic image of a first breast in a first compressed imaging position and acquiring a second mammographic image of the second breast in a second compressed imaging position according to a second view. The image acquisition device processes the first and second mammographic images to compute, for each of the first and second mammographic images, at least one breast volume assessment metric, and then compares the at least one breast volume assessment metric for the first mammographic image to the at least one breast volume assessment metric for the second mammographic image. If the breast volume assessment metrics differ by more than a threshold amount, activating at least one user interface device associated with the image acquisition device that alerts the user of a possible breast positioning error based at least in part upon the difference.

Embodiments related to detecting possible position errors may involve a breast volume assessment metric involving at least one of a total breast volume (Vb), a fibroglandular tissue volume (Vfg), and a ratio (Vfg/Vb) of fibroglandular tissue volume to total breast volume and the same or different views such as one or both of a craniocaudal (CC) view and the second view is a mediolateral oblique (MLO) view. For example, embodiments may involve comparison of different views of the same breast, the same views of different breasts, or different views of different breasts.

Further embodiments are directed to systems that are programmed, configured or operable to implement method embodiments, under technician or user control and/or automatically, and to acquire breast images and/or detect possible patient positioning errors.

For example, one embodiment is directed to a system for acquiring a plurality of images of breast tissue during a scan of the breast tissue that comprises a gantry, an image acquisition device, a controller, a detector and a processor. The gantry supports the image acquisition device, and the controller is coupled to the gantry for controlling a motion parameter of the image acquisition device during an image acquisition. The detector generates at least one image of the object in response to an output of the image acquisition device received at the detector. The processor is in communication with the controller and the detector and is configured to acquire a first image of the breast tissue generated by the detector. The processor is configured to analyze the first image to identify at least one physical characteristic of the breast and to provide data related to the physical characteristic to the controller, which is configured to dynamically modify a selected or pre-determined motion parameter of the image acquisition device that was previously utilized during acquisition of the first image based at least in part upon the physical characteristic data for use in acquiring a plurality of projection images of the breast tissue with the modified motion parameter.

As yet other examples, other system embodiments are directed to detecting possible patient positioning errors and utilizing a 2D projection image to determine whether to proceed with additional 3D projection images.

Further embodiments are directed to computer program products or articles of manufacture comprising a non-transitory computer readable storage medium embodying one or more instructions executable by a computer to perform one or more processes to implement embodiments such as a process for acquiring a plurality of images of breast tissue during a scan of the breast tissue by an image acquisition device, acquiring a 2D projection image to determine whether to acquire multiple 3D projection images and which imaging modality to utilize, and/or detecting a possible patient positioning error.

In a single or multiple embodiments, one particularly advantageous set of measured breast tissue characteristics to use in selecting image acquisition parameters such as a motion parameter includes one or more breast density characteristics derived from a computed physical description of the breast tissue. In a single or multiple embodiments, the breast density characteristics can be processed on a localized, regional, and/or breast-wide basis, and the results used to select an optimal set of tomosynthesis image acquisition parameters. In a single or multiple embodiments, the tomosynthesis image acquisition parameters that are tailored to or customized for the measured breast characteristics include the extent of the tomosynthesis imaging arc, the number of projection images, the gantry angular velocity or overall gantry sweep time, and/or per-projection-image exposure time window (exposure window) to provide one or more of improved image quality and reduced imaging dose. The ability to dynamically vary acquisition or processing methods provides for patient and breast customization, thereby providing one or more of (i) improved image quality, and thus an improved ability to identify and assess potential pathologies and abnormalities, and (ii) lower radiation dose, and thus a reduced the risk of long-term adverse health effects due to lifetime accumulated radiation exposure. In a single or multiple embodiments, breast composition characteristics are considered, e.g., not only breast density but also breast tissue parenchymal pattern or distribution.

In a single or multiple embodiments, one or more automatic volume assessments of the breast are computed from the scout image information and processed to detect potential errors in patient positioning. Based on the general principle that measured total breast volume (Vb), measured total breast fibroglandular tissue volume (Vfg), and/or the ratio Vb/Vfg should stay generally the same between two image views such as the CC and MLO views, these metrics are computed for each of the different views and the results are compared. If one or more of the metrics is substantially different between views, then this fact is brought to the attention of the technician, such as by an alarm or other mechanism, to denote that there may have been a positioning error in one or both of the views. In still other single or multiple embodiments, similar comparisons can be performed in a contralateral context (i.e., left breast versus right breast) and substantial discrepancies brought to the attention of the technician for similar quality assurance purposes.

In a single or multiple embodiments, the first image and the plurality of projection images are acquired with the same image acquisition device, which may be a single or multi-modality image acquisition device or an acquisition device that can acquire different types of images or using different imaging methods. In this manner, the first or scout image and the plurality of other projection images may be acquired with the same imaging device, different imaging devices, and using the same or different imaging modalities. For this purpose, the image acquisition device may be operable to use different imaging modalities and may automatically switch to a different imaging modality or recommend to the user or technician that another imaging modality or imaging device should be utilized, if it is determined that other images are to be acquired. According to one embodiment, the first image and the plurality of projection images are acquired with an x-ray imaging device such as a tomosynthesis x-ray imaging device. According to another embodiment, the first image is acquired with a tomosynthesis x-ray imaging device, and that first image is used to determine or recommend what other imaging procedure to execute.

In a single or multiple embodiments, one or multiple motion parameters such as sweep angle or sweep speed are modified dynamically during a scan of a particular patient in real-time. Other parameters may also be modified including an exposure parameter such as one or more of an exposure window, an exposure voltage or and an exposure number. Thus, the first or scout image is not a calibration image and instead is an image acquired during a scan of the same patient.

In a single or multiple embodiments, the first image that is acquired uses a low dose x-ray, e.g., lower than a normal mammogram exposure. For example, the first radiation dose used to generate the first image can be expressed as $Df=Dp*1/(1+N)$, wherein Df=the first radiation dose, Dp=a total radiation dose of the plurality of projection images, and N=a number of the plurality of projection images. Thus, in this embodiment, the first image dose may be substantially smaller than the subsequent images individually and/or collectively. For example, the first image dose may be substantially less than a radiation dose used to generate a tomosynthesis total scan or standard 2D mammography exposure.

In a single or multiple embodiments, the physical characteristic of the breast tissue that is processed or analyzed is the density or thickness of the breast tissue. The image acquisition device (or processor, controller or computer thereof or associated therewith) determines the density based at least in part upon a physical description of the breast tissue expressed as Vfg, Vb and Vfg/Vb, wherein Vfg=a volume of fibroglandular the breast tissue, and Vb=a volume of the breast tissue. With this data, in certain embodiments, a controller can look up density data within a table or other resource to identify at least one imaging modality (which may be the same or different than the imaging modality used to acquire the first image that was analyzed) based on whether the density data satisfies pre-determined criteria or a threshold value. For example, the table may include data that associates different imaging modalities with their respective density data such that the system can automatically proceed with or recommend the other imaging modalities, which may be supported by the same or different image acquisition device.

Additional inventions that are disclosed and described herein include, but are not limited to:

A computer-implemented method for acquiring a plurality of images of breast tissue during a scan of the breast tissue by an image acquisition device, the method comprising: a computer-controlled image acquisition device acquiring a first image of the breast tissue; the image acquisition device processing the first image to determine a physical characteristic of the breast tissue; the image acquisition device modifying at least one operating parameter that was previously utilized during acquisition of the first image based at least in part upon the physical characteristic, the at least one modified operating parameter comprising a motion parameter of the image acquisition device; and the image acquisition device acquiring a plurality of projection images of the breast tissue using the modified motion parameter.

The image acquisition device determining whether a plurality of additional images of the breast issue should be acquired; and the image acquisition device acquiring the plurality of other images if it is determined that the plurality of other images should be acquired.

The first image and the plurality of projection images being acquired with an image acquisition device comprising a multi-modality image acquisition device.

The image acquisition device determining whether a plurality of additional images of the breast issue should be acquired; and the image acquisition device identifying at least one imaging modality of a plurality of imaging modalities and acquiring the plurality of other images using the at least one identified imaging modality if it is determined that the plurality of other images should be acquired.

The first image and the plurality of projection images being acquired with a computer-controlled image acquisition device comprising an x-ray imaging device.

The first image and the plurality of projection images being acquired with the image acquisition device comprising a tomosynthesis x-ray imaging device.

The first image being acquired using a first imaging modality, and the plurality of additional images being acquired using a second imaging modality that is different than the first imaging modality.

The first image comprising a two dimensional projection image of the breast tissue, and the plurality of additional images comprising three dimensional projection images of the breast tissue.

The image acquisition device determining that the second imaging modality should be utilized to acquire the plurality of additional images based at least in part upon the physical characteristic of the breast tissue satisfying pre-determined criteria.

The physical characteristic comprising a density of the breast tissue that is determined by the image acquisition device based at least in part upon the first image, the image acquisition device identifying at least one imaging modality based at least in part upon comparing the determined breast density and a threshold density value.

The image acquisition device determining the density based at least in part upon a physical description of the breast tissue comprising Vfg, Vb and Vfg/Vb, wherein Vfg=a volume of fibroglandular the breast tissue, and Vb=a volume of the breast tissue.

The image acquisition device performing a lookup in a table to identify the at least one imaging modality, wherein different imaging modalities are associated with respective density data in the table.

Modifying the at least one operating parameter further comprising modifying at least one exposure parameter, the at least one exposure parameter comprising at least one of an exposure window, an exposure voltage or and an exposure number.

The motion parameter comprising at least one of a sweep angle and a sweep speed of the image acquisition device.

The characteristic of the breast tissue comprising a density, a thickness or a composition of the breast tissue.

The first image being generated by the image acquisition device emitting a first radiation dose that is substantially less than a radiation dose of the plurality x-rays used to generate respective projection images.

The first radiation dose is expressed as Df=Dp*1/(1+N), wherein Df=the first radiation dose; Dp=a total radiation dose of the plurality of x-rays used to generate the plurality of projection images; and N=a number of the plurality of projection images.

The first image is not a calibration image, and the first image and the plurality of projection images are images of the same breast tissue of the same patient.

The first image is not a calibration image, and the first image and the plurality of projection images are images acquired in real time during the same scan of the same breast tissue of the same patient.

The image acquisition device dynamically modifying the at least one motion parameter in real time during the same scan of the same breast tissue of the same patient.

The image acquisition device automatically modifying the at least one operating parameter without input by a user of the image acquisition device.

A computer-implemented method for acquiring a plurality of images of breast tissue during a scan of the breast tissue by an image acquisition device, the method comprising: a computer-controlled image acquisition device acquiring two dimensional projection image of the breast tissue; the image acquisition device processing the two dimensional projection image to determine a physical characteristic of the breast tissue; the image acquisition device determining whether a plurality of three dimensional projection images of the breast issue should be acquired based at least in part upon the physical characteristic; and the image acquisition device acquiring the plurality of three dimensional projection images if it is determined that the physical characteristic satisfies pre-determined criteria.

The physical characteristic comprising a density of the breast tissue.

The image acquisition device determining the density based at least in part upon a physical description of the breast tissue comprising Vfg, Vb and Vfg/Vb, wherein Vfg=a volume of fibroglandular the breast tissue, and Vb=a volume of the breast tissue.

A method for acquiring a plurality of images of breast tissue during a scan of the breast tissue by an image acquisition device, the method comprising: a computer-controlled first image acquisition device acquiring a first image of the breast tissue using a first imaging modality; the first image acquisition device processing the first image to determine a physical characteristic of the breast tissue; the first image acquisition device determining that a plurality of projection images should be acquired using at least one of a second imaging modality different than the first imaging modality, and a second image acquisition device different than the first image acquisition device; and the first image acquisition device notifying an operator of the first image acquisition device that a plurality of additional images should be acquired using at least one of the second imaging modality and the second image acquisition device.

The operator being notified that the plurality of additional images should be acquired using the second imaging modality and the first image acquisition device.

The operator being notified that the plurality of additional images should be acquired using the second imaging modality and the second image acquisition device.

BRIEF DESCRIPTION OF THE DRAWINGS

FIG. 4 illustrates a conceptual diagram of a tomosynthesis imaging arc and a table of image acquisition parameters that may be determined according to one or more measured characteristics of a breast as derived from a scout image thereof according to one embodiment.

DETAILED DESCRIPTION OF ILLUSTRATED EMBODIMENTS

Figure 1:
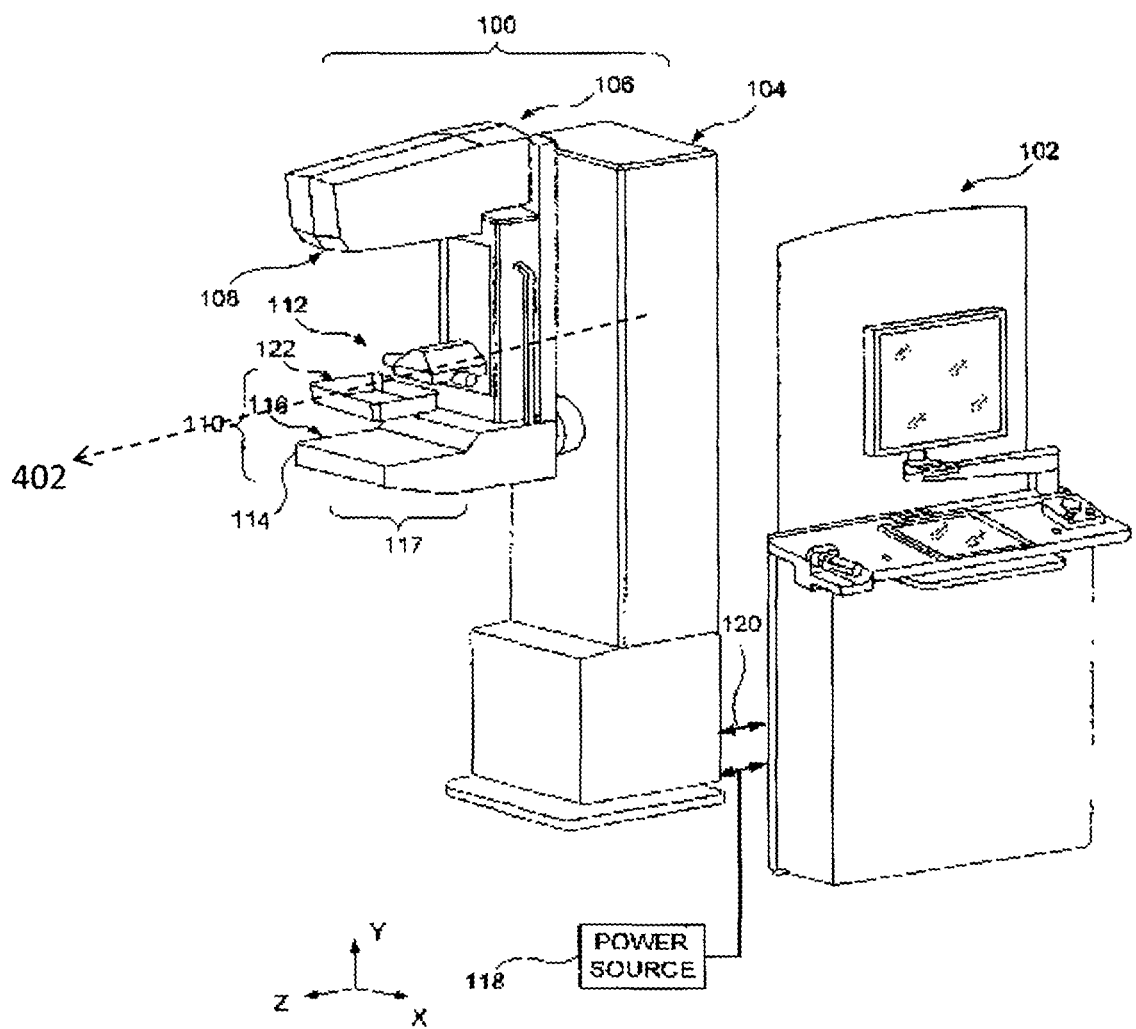
FIG. 1 is a perspective view of a system constructed according to one embodiment and including a gantry and an acquisition workstation.

Systems, methods and computer program products embodied in non-transitory media for dynamically modifying an operating parameter of an image acquisition device, such as a tomosynthesis breast imaging device, is described herein. The operating parameter in one embodiment an image acquisition parameter advantageously selected and derived or modified in response to a measured characteristic of an imaged object such as an imaged breast, and thus tailored to provide the highest quality image for the particular breast. For example, embodiments may be used to improve image quality in a breast tomosynthesis system by dynamically varying operating parameters of the tomosynthesis system in response to physical characteristics of the breast to be imaged (determined during image acquisition in real-time during a scan of the same patient), such as the breast thickness or the breast density. The ability to dynamically vary acquisition or processing methods in real-time during a patient scan helps to customize the system for each particular patient, thereby improving image quality and thus the ability to identify and assess potential pathologies and abnormalities.

Parameters that may be varied in response to physical characteristics may include, but are not limited to, exposure parameters (including number of acquired projection images, duration of exposure, voltage or current used for exposure, etc.) and/or motion parameters (such as sweep angle, sweep speed, etc.). For example, existing tomosynthesis imaging systems are designed to obtain a fixed number of projection images as the x-ray source moves along a sweep angle (e.g., between −15 and +15 degrees) over a predetermined time period which is based on an exposure window for each projection image. In existing systems such parameters are fixed, regardless of any differences in the physical characteristics of the breast being imaged. According to certain embodiments, particular acquisition parameters related to certain physical characteristics of the imaged breast are dynamically modified in order to improve image quality. For example, when imaging a large or very radiodense breast, the x-ray tube current mAs for each of the projections may need to be large so as to adequately penetrate the breast. As the mAs are increased, however, focal spot blurring caused by the longer exposures can degrade image quality. One technique for mitigating the deleterious effects of large mAs and concomitant blurring is to reduce the scan speed of the x-ray source. Alternatively, the number of projection images may be increased to assist in distinguishing architectural distortions.

Other embodiments are related to detecting possible object positioning errors, e.g., detecting possible positioning errors of the same breast by analyzing different views of the same breast, or by analyzing images of different breasts. Further aspects of embodiments and other embodiments and variations thereof are described in further detail with reference to FIGS. 1-4, which describe embodiments in which the object being imaged is a breast of a patient.

FIG. 1 illustrates an embodiment of an image acquisition device or system in the form of a tomosynthesis acquisition system that is configured, programmed or adapted to modify at least one acquisition parameter in response to breast density or thickness characteristics. In the illustrated embodiment, the system includes a gantry 100 and a data acquisition work-station 102. Gantry 100 includes a housing 104 supporting a tube arm assembly 106 rotatably mounted thereon to pivot about a horizontal axis 402 and carrying an x-ray tube assembly 108. X-ray tube assembly 108 includes (1) an x-ray tube generating x-ray energy in a selected range, such as 20-50 kV, at mAs such as in the range 3-400 mAs, with focal spots such as a nominal size 0.3 mm large spot and nominal size 0.1 mm small spot, (2) supports for multiple filters such as molybdenum, rhodium, aluminum, copper, and tin filters, and (3) an adjustable collimation assembly selectively collimating the x-ray beam from the focal spot in a range such as from 7×8 cm to 24×29 when measured at the image plane of an x-ray image receptor included in the system, at a maximum source-image distance such as 75 cm. Also mounted on housing 104, for rotation about the same axis 402, is a compression arm assembly 110 that comprises a compression plate 122 and a receptor housing 114 having an upper surface 116 serving as a breast plate and enclosing a detector subsystem system 117 comprising a flat panel x-ray receptor, a retractable anti-scatter grid and a mechanism for driving and retracting anti-scatter grid (not shown) as described in U.S. Pat. No. 7,443,949 entitled "Mammography system and method employing offset compression paddles, automatic collimation, and retractable anti-scatter grid" filed Oct. 17, 2002 by the assignee hereof, the contents of which are incorporated herein by reference.

Housing 104 also encloses a vertical travel assembly for moving tube arm assembly 106 and compression arm assembly 110 up and down to accommodate a particular patient or imaging position and a tube arm assembly rotation mechanism 406 to rotate tube arm assembly 106 about axis 402 along different sweep angles to different imaging positions. A detector subsystem may include a rotation mechanism 408 for rotating components of detector subsystem 117 (such as x-ray receptor 502) about axis 402 to accommodate different operations modes, and couple/uncouple mechanism 410 to selectively couple or uncouple tube arm assembly 106 and compression arm assembly 110 to and from each other, and tube arm assembly 106 and detector subsystem 117 to and from each other. Housing 104 also encloses suitable motors and electrical and mechanical components and connections to implement the functions discussed here.

Work-station 102 may comprise components similar to those in the SELENIA mammography system, including a display screen (typically a flat panel display that may include touch-screen functionality), user interface devices such as a keyboard, possibly a touch-screen, and a mouse or trackball, and various switches and indicator lights and/or displays. SELENIA is a registered trademark of Hologic Inc., Bedford, Mass. Work-station 102 may also include computer facilities similar to those of the SELENIA system (but adapted through hardware, firmware and software differences) for controlling gantry 100 and for processing, storing and displaying tomosynthesis data received from gantry 100. A power generation facility for x-ray tube assembly 108 may be included in housing 104 or in work-station 102. A power source 118 powers work-station 102. Gantry 100 and work-station 102 exchange data and controls over a schematically illustrated connection 120.

Additional storage facilities can be connected to work-station, such as one or more optical disc drives for storing information such as previously obtained images and software, or a local printer (not shown). In addition, the disclosed system can be connected to a hospital or local area or other network and through the network to other systems such as a soft copy workstation, a Computer Aided Detection (CAD) station, a technologist workstation and other imaging systems or output devices.

In standard mammography mode, typically used for screening mammography, tube arm assembly 106 and compression arm assembly 110 are coupled and locked together in a relative position such as seen in FIG. 1, such that an x-ray beam from x-ray tube assembly 108 illuminates x-ray receptor when the patient's breast is compressed by compression device 112. In this mode, the system operates in a manner similar to said SELENIA system to take a mammogram. A vertical travel assembly and tube arm rotation mechanism can make vertical adjustments to accommodate a patient, and can rotate tube arm assembly 106 and compression arm assembly 110 together as a unit about an axis for different image orientations such as for CC and for MLO images. For example, tube arm assembly 106 and compression arm assembly 110 can rotate between (−195 degrees) and (+150 degrees) about the axis.

In tomosynthesis mode, tube arm assembly 106 and compression arm assembly 110 are decoupled such that compression arm assembly 110 stays in one position, compressing the patient's breast, while tube arm assembly 106 rotates about the axis, for example +/−15 degrees relative to compression arm assembly 110. Tomosynthesis can be carried out for different image orientations, so that compression arm assembly 110 can be rotated about the axis (alone or together with assembly 106) for a desired image orientation and locked in place, and then tube arm assembly 106 can be rotated relative to that position of compression arm assembly 110 for tomosynthesis imaging over +/−15 degrees or some other desired angular range.

For example, as mentioned above according to one aspect, the angular range of the tomosynthesis sweep can be varied according to characteristics of the imaged breast. In addition image exposure parameters including number of acquired projection images, duration of exposure, voltage or current used for exposure can also be dynamically varied in accordance with the particular composition of the imaged breast.

While certain embodiments are described with reference to a mammography/tomosynthesis system, it will be understood that embodiments may involve an image acquisition system that is capable of or that utilizes other imaging modalities and combinations thereof. For example, while embodiments may be implemented using a combination mammography/tomosynthesis machine, embodiments may also involve a stand-alone tomosynthesis acquisition system or stand alone mammography system. Moreover, while certain embodiments are described with general reference to x-ray and tomosynthesis imaging acquisition devices, embodiments may involve one or more and various combinations of handheld and robotic imaging modalities including 2D x-ray projection imaging, tomosynthesis x-ray projection imaging, 3D breast ultrasound, robotic-guidance targeted local 2D and 3D breast ultrasound, magnetic resonance imaging, positron emission mammography, breast specific gamma imaging, and other imaging modalities in order to acquire images for use in embodiments. Further, as described in further detail below, various types and combinations of imaging modalities may be utilized for image acquisition, and embodiments may involve automatically acquiring images using the same or one or more other modalities or recommending to a technician or user that another imaging system or modality, which may be the same or different than the imaging modality, should be utilized. Further, embodiments may involve an initial 3D projection image to determine whether to proceed with additional 2D projection images or an initial 2D projection image to determine whether to proceed with additional 3D projection images. For ease of explanation, reference is made to x-ray imaging, e.g., mammography and tomosynthesis, and to a first or scout image that is a 2D projection image and subsequent 3D projection images as examples of how embodiments may be implemented.

Figure 2:
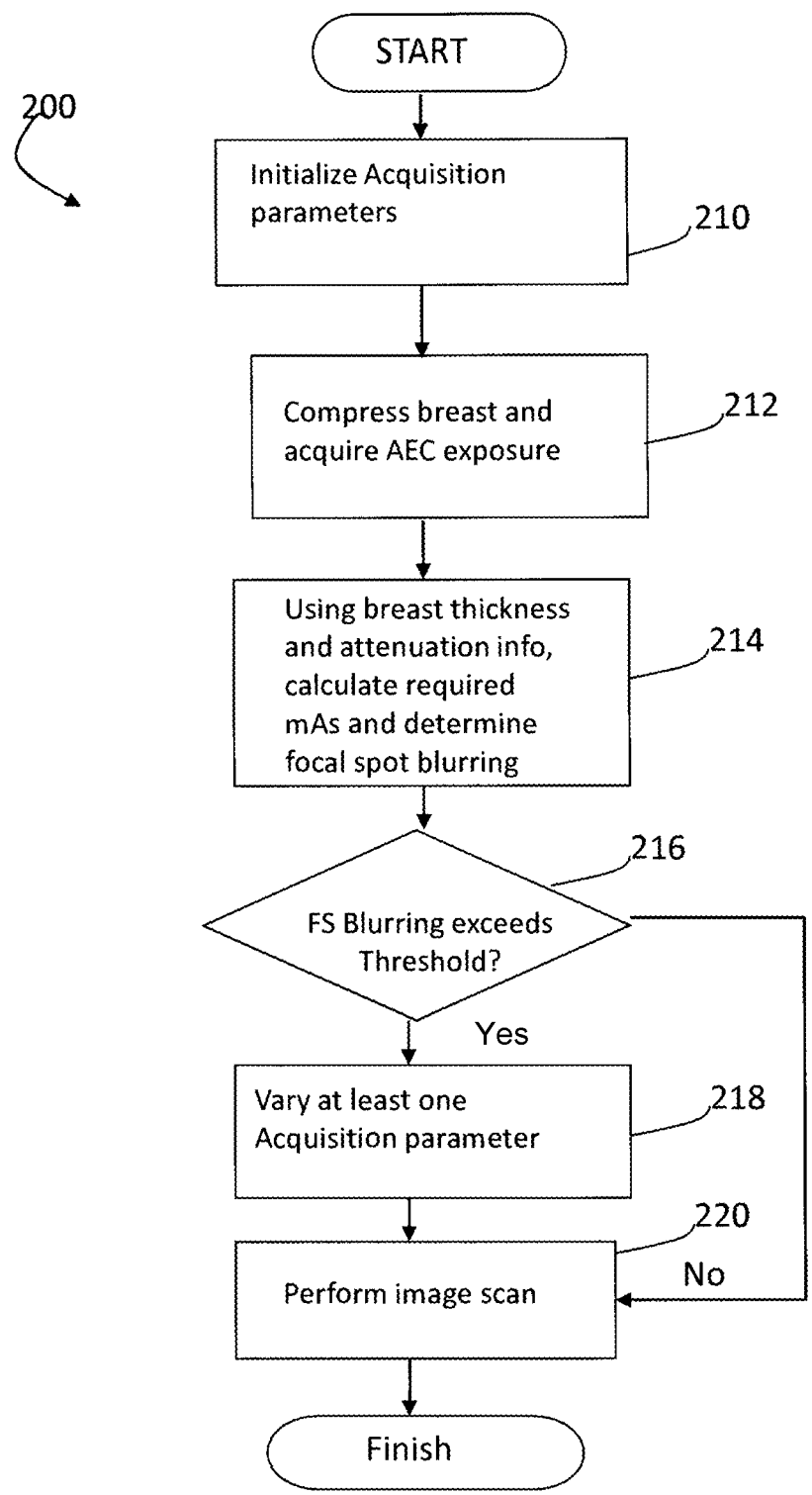
FIG. 2 is a flow diagram illustrating one embodiment of a method for dynamically modifying image acquisition parameters based on a physical characteristic of an imaged object such as imaged breast tissue.

Referring to FIG. 2, one embodiment of a process 200 for dynamically setting image acquisition parameters may be implemented or executed by a controller, processor and/or computer of, utilized or accessed by the image acquisition system or components thereof shown in FIG. 1. At step 210 image acquisition parameters are initialized. In particular the acquisition parameters are set to those used to capture an Automatic Exposure Control (AEC) (or "scout") image of the breast, where a first or scout image (generally, "scout" image) is an x-ray is taken (either at a low dose, or full dose) and the image receptor's image is read by a processor or controller as part of a computer process.

At step 212, the breast is compressed and the scout image is obtained. The computer process uses information from the scout image to identify the breast's radio-density and to calculate the optimal x-ray tube exposure voltage kVp, current mAs, and exposure time for delivering a desired x-ray dose.

A variety of methods can be used to determine breast radio-density. For example, the overall density of the breast can be determined by finding the mean density of the breast from the pixel values of the breast image by adding all pixel values and dividing the result by the number of pixel values. Other ways of deriving breast characteristics, including density, from breast image are discussed by Highnam, Brady, and Shepstone in "Mammographic Image Analysis", Eur. J. Radiologic, 1997 January; 24(1)20-32, incorporated herein by reference. Additional methods of determining breast density are described in U.S. Patent Application US 2007/0274585 and U.S. Pat. No. 5,657,362, each of which is also incorporated herein by reference as through set forth in full. Alternative methods of determining breast thickness can also be used. Various methods take into account the distance between compression paddles and the force used to reach a desired compression.

With continuing reference to FIG. 2, at step 214, information associated with the identified mA and exposure time may be used to determine the potential extent of focal spot blur. Should it be determined at step 216 that the potential focal spot blur exceeds a desired threshold, at step 218 at least one acquisition parameter is modified in response to the breast density and/or breast thickness information to either reduce focal spot blur (for example, by increasing mA and reducing the exposure window), compensate for focal spot blur (for example by increasing the number of projection images for varying the sweep angle), or meet some other imaging goal (such as reducing exposure). At step 220 the image is then acquired using the customized acquisition parameters. It can be appreciated that the selection of which acquisition parameter to vary to meet a desired goal (and even the desired goal itself) is can be based on analytical and/or empirical determinations in the design of the system for promoting an optimal balance of high image quality and reduced radiation dose, and may differ depending upon the particular breast composition.

For example, for 'fatty' breast it may be more desirable to reduce mA and increase the exposure window, while for 'dense' breasts it is more desirable to increase mA, reduce the exposure window and/or obtain additional projection images. In one embodiment, a pre-populated lookup table may be provided that outputs desired acquisition parameters based on thickness and/or density information. This pre-populated lookup table may be stored in a computer storage medium, capable of being updated as desired, for example based on a particular population or improved data. Alternatively, received density and/or thickness information may be dynamically processed using pre-programmed or dynamically programmed algorithms for dynamic selection of acquisition parameters for tomosynthesis imaging. A person skilled in the art would be able to realize such lookup table, based on analytical and/or empirical data and other information known to the skilled artisan, without undue experimentation in view of the present disclosure.

Figure 3:
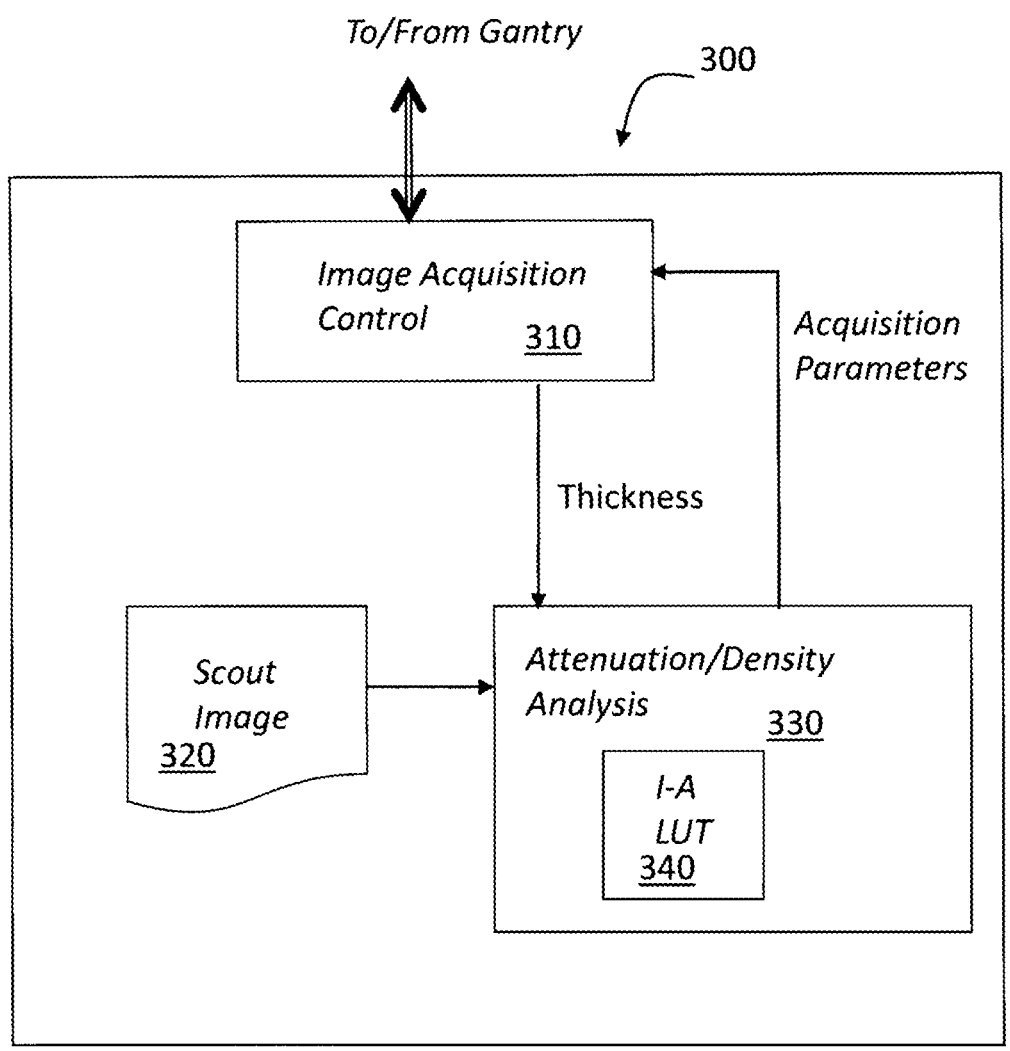
FIG. 3 illustrates a block diagram of system components or software modules and data structures that may be used to implement embodiments and that may be stored in a computer readable media of, utilized or accessed by an acquisition workstation.

FIG. 3 illustrates several components that may be included in one embodiment of a control system 300 for controlling the acquisition of projection images by a breast tomosynthesis system. Control system 300 includes a plurality of components which may be implemented in hardware, software or a combination thereof. Control system 300 includes acquisition controller 310 which provides signals for controlling the x-ray tube, including information for controlling the number of projection images, sweep angle for the tube arm, exposure window, mA and voltages of each exposure, and other motion and exposure parameters. A memory, database or other storage device in control system 300 stores the scout image 320, which is in one embodiment a 2D projection image comprising a plurality of pixels having intensities which represent the x-ray attenuation values at the various points in the image. Attenuation/density analysis unit or processor 330 includes, utilizes or accesses a Look Up Table (LUT) 340 that may also be stored in memory, database or other storage device and analyzes attenuation information from scout image 320 to determine a breast density using any of the methods described above.

The attenuation/density analysis unit or processor 330 access or utilize the LUT 340 to receive as an input, read, determine or derive density information and/or breast thickness information (for example, as received from the acquisition controller 310 in response to compression plate relative distance and compression force) to provide breast tomosynthesis acquisition parameters for obtaining optimal tomosynthesis images for the particular breast composition.

Accordingly, a system and method for dynamically selecting or identifying and modifying an image acquisition parameter for use in tomosynthesis breast imaging provides in response to a measured characteristic of an imaged breast allows for a tailored and customized set of operating parameters, thus providing the highest quality image for the particular breast composition.

FIG. 4 illustrates a conceptual diagram of a tomosynthesis imaging arc traversed by the x-ray source of a tomosynthesis imaging system, and a table 420 of image acquisition parameters that may be determined (e.g. according to a LUT) according to one or more measured characteristics derived from a scout image thereof according to a preferred embodiment. Shown in FIG. 4 is an x-ray point source 402 mounted on a gantry (not shown), the system being configured to acquire "N" tomosynthesis projection images over a tomosynthesis imaging arc $\theta_T$ encompassing "N" respective angular locations 404. The tomosynthesis imaging arc $\theta_T$ is traversed in an overall gantry sweep time T. During the continuous angular sweep, the x-ray imaging source 402 is kept off except in an angular interval $\Delta\theta_i$ around each projection imaging location, where it is activated at a predetermined tube current (mA) and operating voltage (kVp) for a time interval $\Delta t_i$, termed an exposure window, resulting in a milliamp seconds metric ($mAs_i$) for each projection image and, for N projection images, an overall milliamp seconds metric ($mAs_T$) of N times ($mAs_i$). The total radiation dose to the patient for the tomosynthesis imaging sweep is proportional to the total milliamp seconds metric $mAs_T$. As known in the art, the total radiation dose also increases as kVp increases. The amount of focal spot blurring is directly proportional to angular interval $\Delta\theta_i$, and so this arc, which is equal to the angular velocity of the gantry x exposure window, can be called a "blur angle" as denoted in FIG. 4.

According to one embodiment, a scout image of the breast, as properly positioned and compressed between compression paddles, is acquired by the tomosynthesis imaging system with the x-ray source positioned either at zero degrees (i.e., in the middle of the imaging arc at a position corresponding to a standard 2D mammography projection image), or at a predetermined offset angle from zero degrees. The parameters for the scout image are configured such that the overall radiation dose is approximately 1/(1+N) times the conventional 2D mammography projection image dose, where N is the nominal number of tomosynthesis projection images for an average-sized breast having average density characteristics. By way of example, the tomosynthesis imaging system may have a nominal number of 15 projection images (N=15) that are taken over a nominal tomosynthesis imaging arc of 15 degrees, the x-ray source being rotated from −7.5 degrees to 7.5 degrees. As would be appreciated by the skilled artisan in view of the present disclosure, the term "nominal" is used here because the system according to the present invention can operate at multiple different values for the number of projection images depending on the breast characteristics, but will generally have a default or starting configuration designed for the average expected breast characteristics. For purposes of example only and not by way of limitation, where a typical radiation dose for an average breast might be 1.6 mGy for standard 2D projection mammography, the dose for the scout image would be on the order of 0.1 mGy. Thus, according to one embodiment, the dose of the scout image is substantially less than the dose of the plurality of projection images individually and collectively. The dose of the scout image may be sufficiently low such that a physical attribute of breast tissue imaged in a scout image can be analyzed by a processor, but is not readable or meaningfully discernable by a user or technician of the image acquisition system.

Upon acquisition, the scout image is then processed or analyzed according to one or more of the above-described methods, such as the Highnam & Brady method, to generate a two-dimensional array that characterizes, for each pixel, the total columnar height of fibroglandular tissue (in cm) for that pixel location (alternatively the height can be expressed as a percentage of the paddle separation distance. Thus, for example, where the compression paddles are separated by 4 cm, the algorithm might compute, for one pixel location, a fibroglandular tissue height of 1.4 cm, meaning that there is a total of 1.4 cm of fibroglandular tissue and 2.6 cm of fat between the compression paddles above that pixel location, and might compute, for another pixel location, a fibroglandular tissue height of 0.7 cm, meaning that there is a total of 0.7 cm of fibroglandular tissue and 3.3 cm of fat between the compression paddles for that other pixel location. This two-dimensional array can be called a "physical description image" or "physical description" of the breast.

For one preferred embodiment, the physical description image can be processed (based, for example, on known attenuation coefficients for fibroglandular tissue versus fat tissue) to determine a region (for example, a region of a predetermined size such as a 1 cm-radius circle) for which there will be maximum average attenuation, and then the acquisition parameters can be determined based on that maximum attenuation region and value (using, for example, the lookup table method described above). In an alternative preferred embodiment, there may be computed overall breast volumetric density assessment metrics or other biomarker derived from the physical description of the breast (or similar breast density mapping algorithm), which is provided as an input to a breast volumetric assessment software package or system such as Quantra™, which computes one or more such metrics and is available from Hologic Inc., Bedford, Mass. Further details regarding the Quantra™ system are described in "Understanding R2 Quantra 1.3," PN MAN-01224 Rev 001, Hologic, Inc. (2009), the contents of which are incorporated herein by reference.

For example, the Quantra™ breast volumetric assessment software package may compute and process the physical description of the breast to generate a volume Vfg of fibroglandular tissue (in cubic centimeters or $cm^3$), an overall volume Vb of the breast (in $cm^3$), and then divides the volumes to produce a volumetric fraction Vfg/Vb of breast fibroglandular tissue as a percentage of the overall breast volume. In yet another preferred embodiment, the selection of the image acquisition parameters can be based on a combination of regional density characteristics and the overall breast assessment measures Vfg, Vb, and Vfg/Vb.

For purposes of example only and not by way of limitation, the LUT 340 may be programmed with numerical information that results in the following one or more scenarios. For a "nominal" breast having average expected statistical characteristics, the system may have a default configuration of a 15-degree tomosynthesis imaging arc (i.e., −7.5 degrees to +7.5 degrees), with N=15 tomosynthesis projection images, an overall gantry sweep time of 3 seconds, an exposure window of 100 milliseconds, a tube current of 100 mA, and an operating voltage of 28 kVp (for a 4 cm breast) or 29 kVp (for a 5 cm breast). For this nominal scenario, there is a blur angle of (0.1 sec)(15 degrees/3 sec)=0.5 degrees. However, if the scout imaging process and associated density evaluation indicates a very high breast density (with size and other characteristics staying the same), the lookup table might yield an optimal configuration of a 20-degree tomosynthesis imaging arc (i.e., −10 degrees to +10 degrees), with N=20 tomosynthesis projection images, and an overall gantry sweep time of 4 seconds, the other parameters staying the same. For this scenario, there is advantageously the same blur angle of (0.1 sec)(20 degrees/4 sec)=0.5 degrees, and yet there is a higher overall exposure, a higher number of images, and an increased overall arc provided for sufficiently imaging through the denser tissue. In other alternatives, there can be the same 15-degree sweep angle with N=30 images and the same sweep time of 3 seconds, the other parameters staying the same. On the other hand, if the scout imaging process and associated density evaluation indicates a very low breast density (with size and other characteristics staying the same), the lookup table might yield an optimal configuration of a 15-degree tomosynthesis imaging arc, with N=15 tomosynthesis projection images, an exposure window of 50 ms, and an overall gantry sweep time of 1.5 seconds, the other parameters staying the same. For this scenario, there is the same blur angle, but a much lower dose because that is all that is really needed for the low-density breast. Alternatively or in conjunction the number of projection images can be reduced. It is to be appreciated that there are many different trade-offs and alternative scenarios and sub-scenarios that can be implemented into the lookup table 340 other than the simplified example provided above while remaining well within the scope of the present teachings.

In other embodiments, breast composition characteristics are considered, e.g., not only breast density as discussed above, but also breast tissue parenchymal pattern or distribution.

According to another embodiment, the overall breast assessment metrics are used to alert the radiology technician (or other medical professional who is positioning the patient and operating the image acquisition system) that they may have made a breast positioning error. Generally speaking, for the same physical breast, the breast assessment measures Vfg, Vb, and Vfg/Vb should be similar between two different views. Thus, according to one embodiment, the breast assessment measures Vfg, Vb, and Vfg/Vb can be computed separately for two different views of the same breast (CC and MLO, for example) and then compared with each other. If one or more of these metrics is substantially different for one view compared to the other view, e.g., for the CC view versus the MLO view (for example, greater than 15% difference between the views, or some other threshold different), then this fact and/or an alert of a possible positioning error, is brought to the attention of the technician, because there may have been a positioning error in one or both of the views. Predetermined weightings or expected offsets can be included in the comparison process as needed (for example, to accommodate for the effects on the assessment metrics of the presence of the pectoral muscle in the MLO view versus the CC view, for example). Contralateral comparisons can also be used, since the volumetric assessment metrics for the left and right breasts can also be expected to have some general correspondence.

Other embodiments may involve analysis of different breasts of the same patients. For this purpose, the same view of each breast may be analyzed to determine a possible positioning error of at least breast, or different views of each breast may be utilized. Similar to the method described above, if one or more of these metrics is substantially different for one breast compared to the other and/or for one view compared to the other view, then this fact and/or an alert of a possible positioning error, is brought to the attention of the technician, because there may have been a positioning error in one or both of the views.

Having described various embodiments of the invention, it should be appreciated that the above specific examples and embodiments are illustrative, and many variations can be introduced on these examples and embodiments without departing from the spirit of the disclosure or from the scope of the appended claims. For example, elements and/or features of different illustrative embodiments may be combined with each other and/or substituted for each other within the scope of this disclosure and appended claims. In addition, certain flow diagrams have been used to describe various processes, it should be appreciated that the processes can be performed in hardware, software, or a combination thereof. The software may comprise a plurality of program code and data structures which are stored in a computer readable medium local to or remote from the tomosynthesis image acquisition system, and may generally be used to transform the acquired scout image information into physical control signals for controlling image capture.

Moreover, while certain embodiments are described above with reference to a scout image and subsequent projection images acquired using a tomosynthesis system, the system may involve an initial analysis of a scout image and whether additional projection images should be acquired, and if so, which imaging modalities and/or imaging systems should be utilized for acquiring additional images following the scout image.

For example, according to one embodiment, if by the scout image the breast is found to be very low-density (below a certain threshold) and yet the clinic work order has called for tomosynthesis, the system can automatically "prohibit" the tomosynthesis process from taking place, because it is not needed. Conversely, according to another embodiment, if by the scout image the breast is found to be very high-density (above a certain threshold) and yet the clinic work order has not called for tomosynthesis, the system can automatically "strenuously recommend" or even automatically initiate the tomosynthesis process or one or more other imaging modalities because it is needed.

In another embodiment, a scout image may be acquired, and the system may automatically proceed to modify a motion parameter based on a physical characteristic of the beast derived from the account and then acquire projection images using the same imaging modality that was utilized to acquire the scout image. Thus, the scout and subsequent projection images can be acquired in real time during the scan of the same patient, while selected motion or other parameters are dynamically modified on the fly during the scan, without requiring the user or technician to manually adjust the motion or other operating parameters and/or manually confirm or authorize acquisition of additional projection images. In another embodiment, additional projection images are acquired after confirmation by the technician or user.

According to another embodiment, a scout image may be acquired, and if it is determined that additional images are to be acquired, the system may automatically proceed to acquire or recommend acquisition of projection images using the same imaging modality that was utilized to acquire the scout image. Thus, for example, the initial scout image and the additional projection images can be acquired using the same system and same tomosynthesis imaging modality. According to another embodiment, a scout image may be acquired using a first imaging modality, and if it is determined that additional images are to be acquired, the system may automatically proceed to acquire projection images using another imaging modality determined or identified by the system. For this purpose, a controller or processor of the system may access a lookup table (e.g., as discussed above with reference to FIG. 3) that includes data of a physical characteristic such as breast density or other derived data or characteristics and corresponding imaging modalities such that one or more other imaging modalities may be identified if the physical characteristic data satisfies pre-determined criteria, e.g., based at least in part upon a comparison of the breast density and a pre-determined or threshold density value.

For example, the first or scout image may be a 2D x-ray projection image, and the subsequent images are acquired, or recommended to be acquired, using one or more other imaging modalities such as 3D breast ultrasound, robotic-guidance targeted local 2D and 3D breast ultrasound, magnetic resonance imaging, positron emission mammography, breast specific gamma imaging, and other imaging modalities, Thus, embodiments may involve a scout image such as a two-dimensional projection image followed by acquisition or a recommendation to acquire a plurality of other images such as three-dimensional projection images using the same imaging modality and same image acquisition system, a scout image acquired using a first image modality and an image acquisition system followed by a plurality of other images using another imaging modality and same image acquisition system, a scout image acquired using a first image modality and a first image acquisition system followed by a plurality of other images using another imaging modality and different, second image acquisition system.

Further, although FIG. 3 illustrates several representative components of an acquisition parameter control system, it will readily be appreciated by one of skill in the art that any delineation were made on a functional basis solely for the purpose of simplifying description of a representative embodiment. Moreover, it will be understood that embodiments may be implemented or executed by system components such as a computer, controller, a processor that analyzes physical characteristics such as density, and that such component may be integrated within the system shown in FIG. 1 or accessed by the system. Thus alternative embodiments which include additional functionality, or differently delineated functionality, are to be considered equivalents hereto. Thus the present invention should not be limited by the above description, but rather only by the appended claims.

Whereas many alterations and modifications of the present invention will no doubt become apparent to a person of ordinary skill in the art after having read the foregoing description, it is to be understood that the particular embodiments shown and described by way of illustration are in no way intended to be considered limiting.

For example, while certain embodiments have been described with reference to determining physical characteristic of the breast tissue such as one or more of thickness, density and composition based on an initial 2D projection image to determine whether to acquire additional 3D projection images, embodiments may also involve an initial 3D projection image to determine whether to acquire additional 2D images. It will also be understood that the initial image may be used to utilize or recommend a single or multiple other imaging modalities or use of the same or other image acquisition device.

As a further example, while certain embodiments have been described with reference to determining physical characteristic of the breast tissue such as one or more of thickness, density and composition for determining potential positioning errors, other embodiments may involve a comparison of a view from a present study with a view from a prior study (a temporal comparison). In such embodiments in which the comparison is temporal, then the current value may be larger than the prior. In such cases, the positioning may be better that that of the prior such that more tissue is pulled into view onto a detector. However, if the value for the current is smaller than that of the prior, then the positioning may be worse such that less tissue is pulled onto the detector.

Further, where methods and steps described above indicate certain events occurring in certain order, those of ordinary skill in the art having the benefit of this disclosure would recognize that the ordering of certain steps may be modified and that such modifications are in accordance with the variations of the invention. Additionally, certain of the steps may be performed concurrently in a parallel process as well as performed sequentially. Thus, the methods shown in various flow diagrams are not intended to be limited to a particular sequential order, unless otherwise stated (e.g., a scout image preceding other images) or required.

Accordingly, embodiments are intended to exemplify alternatives, modifications, and equivalents that may fall within the scope of the claims.

What is claimed is:

1. A computer-implemented method, comprising:
    a medical imaging system, by an image acquisition workstation, processing an image of a subject's breast tissue acquired in a prior study of the subject's breast tissue to determine a value corresponding to a physical characteristic of the subject's breast tissue as of the time of the prior study;
    the medical imaging system, by an imaging device in communication with the image acquisition workstation and comprising a radiation emitter, acquiring a new image of the subject's breast tissue by activation of the radiation emitter;
    the medical imaging system, by the image acquisition workstation,
        processing the new image to determine a present value corresponding to the physical characteristic of the subject's breast tissue,
        comparing the value corresponding to the physical characteristic determined from the image acquired in the prior study with the present value corresponding to the physical characteristic determined from the new image, and
        determining at least one operating parameter of the imaging device based at least in part upon a difference between the value of the physical characteristic as of the time of the prior study with the present value of the physical characteristic; and
    the medical imaging system, by activation of the radiation emitter of the imaging device, acquiring one or more additional new images of the subject's breast tissue using the determined at least one operating parameter.

2. The method of claim 1, wherein the physical characteristic is selected from the group consisting of a density, a thickness, a volume and a composition of the subject's breast tissue.

3. The method of claim 1, wherein the imaging device, by activation of the radiation emitter, acquires projection images of the subject's breast tissue using an imaging modality selected from the group consisting of 3D breast ultrasound, robotic-guidance targeted local 2D and 3D breast ultrasound, magnetic resonance imaging, positron emission mammography, and breast specific gamma imaging.

4. The method of claim 1, further comprising the medical imaging system, by the image acquisition workstation, determining whether one or more additional new images of the subject's breast tissue should be acquired based at least in part upon the difference between the value corresponding to a physical characteristic of the subject's breast tissue as of the time of the prior study and the present value corresponding to the physical characteristic.

5. The method of claim 4, wherein the physical characteristic is selected from the group consisting of a density, a thickness, a volume and a composition of the subject's breast tissue.

6. The method of claim 1, the imaging device comprising a tomosynthesis acquisition device and the radiation emitter comprising an x-ray tube, wherein the medical imaging system, by the tomosynthesis acquisition device, acquires the new image by activation of the x-ray tube.

7. The method of claim 6, wherein the new image is acquired by the x-ray tube generating x-ray energy at about 20 kv to about 50 kv, at about 3 mAs to about 400 mAs and with a focal spot of about 0.1 mm to about 0.3 mm.

8. The method of claim 6, wherein the new image is generated by the x-ray tube moving along a sweep angle over a pre-determined time period.

9. The method of claim 1, the imaging device comprising an x-ray imaging device, wherein the radiation emitter is an x-ray tube of the x-ray imaging device, wherein the medical imaging system, by the x-ray imaging device, acquires the new image by activation of the x-ray tube.

10. The method of claim 1, wherein the medical imaging system customizes image acquisition parameters of the radiation emitter based at least in part upon the difference in the value of the physical characteristic as of the time of the prior study and the present value of the physical characteristic.

11. The method of claim 1, wherein the medical imaging system automatically modifies at least one operating parameter of the radiation emitter of the imaging device without input by a user of the imaging device.

12. The method of claim 2, wherein the physical characteristic is the volume of the subject's breast tissue, and the medical imaging system, by the image acquisition workstation, determines the volume of the subject's breast tissue based at least on a volume metric selected from the group consisting of a total breast tissue volume, a fibroglandular tissue volume, and a ratio of fibroglandular tissue volume to the total breast volume.

13. The method of claim 12, wherein the volume metric is determined separately for two different views of the same breast of the subject.

14. The method of claim 12, further comprising the medical imaging system, by the image acquisition workstation, generating a user interface and presenting the user interface to the user through a display of the image acquisition workstation to alert the user of a possible positioning error of the subject's breast tissue based at least in part upon the volume metric of the new image and the volume metric of the image acquired in the prior study.

15. The method of claim 1, further comprising the medical imaging system, by the image acquisition workstation, storing the image of the subject's breast tissue acquired in the prior study to a computer readable storage medium, wherein the image acquisition workstation reads or retrieves the stored image from the computer readable storage medium for determining whether one or more new images of the subject's breast tissue should be acquired.

16. A computer-implemented method, comprising:
a medical imaging system, by an image acquisition workstation,
processing an image of the subject's breast tissue acquired in a prior study of the subject's breast tissue to determine a physical characteristic of the subject's breast tissue as of the time of the prior study, wherein the image from the prior study was acquired using a first imaging modality and a first imaging device, and
determining, based at least in part upon the physical characteristic of the subject's breast tissue as of the time of the prior study, whether one or more new images of the subject's breast tissue should be acquired using at least one of a second imaging modality different than the first imaging modality and a second imaging device different than the first imaging device; and
the medical imaging system, by activation of a radiation emitter of the second imaging device and using the second imaging modality, acquiring one or more new images of the subject's breast tissue based on the physical characteristic of the subject's breast tissue as of the time of the prior study.

17. The method of claim 16, wherein the first imaging modality comprises x-ray projection imaging.

18. The method of claim 17, wherein the second imaging modality is selected from the group consisting of 3D breast ultrasound, robotic-guidance targeted local 2D and 3D breast ultrasound, magnetic resonance imaging, positron emission mammography, and breast specific gamma imaging.

19. The method of claim 16, wherein the physical characteristic is selected from the group consisting of a density, a thickness, a volume, and a composition of the subject's breast tissue.

20. The method of claim 16, the second imaging device comprising a tomosynthesis acquisition device and the radiation emitter comprising an x-ray tube, wherein the second medical imaging system, by the tomosynthesis acquisition device, acquires the one or more new images by activation of the x-ray tube.

21. The method of claim 20, wherein the one or more new images are acquired by the x-ray tube generating x-ray energy at about 20 kv to about 50 kv, at about 3 mAs to about 400 mAs and with a focal spot of about 0.1 mm to about 0.3 mm.

22. The method of claim 20, wherein the one or more new images are generated by the x-ray tube moving along a sweep angle over a pre-determined time period.

23. The method of claim 16, the second imaging device comprising an x-ray imaging device, wherein the radiation emitter is an x-ray tube of the x-ray imaging device, wherein the medical imaging system, by the x-ray imaging device, acquires the one or more new images by activation of the x-ray tube.

24. The method of claim 16, wherein the medical imaging system customizes image acquisition parameters of the second imaging device based at least in part upon the physical characteristic of the subject's breast tissue as of the time of the prior study.

25. The method of claim 16, wherein the medical imaging system automatically modifies at least one operating parameter of the radiation emitter of the second imaging device without input by a user of the second imaging device.

26. The method of claim 16, further comprising the medical imaging system, by the image acquisition workstation, storing the image of the subject's breast tissue acquired in the prior study to a computer readable storage medium, wherein the image acquisition workstation reads or retrieves the stored image from the computer readable storage medium for determining whether one or more new images of the subject's breast tissue should be acquired.

27. A computer-implemented method, comprising:
a medical imaging system, by an image acquisition workstation,
processing an image of the subject's breast tissue acquired in a prior study of the subject's breast tissue to determine a value of a physical characteristic of the subject's breast tissue as of the time of the prior study,
comparing the value corresponding to the physical characteristic determined from the image acquired in the prior study with a pre-determined threshold value, and
determining whether one or more new images of the subject's breast tissue should be acquired based at least in part upon the difference between the value corresponding to a physical characteristic of the subject's breast tissue as of the time of the prior study and the pre-determined threshold value; and
the medical imaging system, by activation of a radiation emitter of an imaging device in communication with the image acquisition workstation, acquiring one or more new images of the subject's breast tissue based on a determination based at least in part upon the difference between the value corresponding to the physical characteristic as of the time of the prior study and the pre-determined threshold value.

28. The method of claim 27, wherein the physical characteristic is selected from the group consisting of a density, a thickness, a volume and a composition of the subject's breast tissue.

29. The method of claim 27, wherein the image acquired in the prior study was acquired using x-ray projection imaging, and wherein the one or more new images are acquired by activation of the radiation emitter and using an imaging modality selected from the group consisting of 3D breast ultrasound, robotic-guidance targeted local 2D and 3D breast ultrasound, magnetic resonance imaging, positron emission mammography, and breast specific gamma imaging.

30. The method of claim 27, the imaging device comprising a tomosynthesis acquisition device and the radiation emitter comprising an x-ray tube, wherein the medical imaging system, by the tomosynthesis acquisition device, acquires the one or more new images by activation of the x-ray tube.

31. The method of claim 30, wherein the one or more new images are acquired by the x-ray tube generating x-ray energy at about 20 kv to about 50 kv, at about 3 mAs to about 400 mAs and with a focal spot of about 0.1 mm to about 0.3 mm.

32. The method of claim 30, wherein the one or more new images are generated by the x-ray tube moving along a sweep angle over a pre-determined time period.

33. The method of claim 27, the imaging device comprising an x-ray imaging device, wherein the radiation emitter is an x-ray tube of the x-ray imaging device, wherein the medical imaging system, by the x-ray imaging device, acquires the one or more new images by activation of the x-ray tube.

34. The method of claim 27, wherein the medical imaging system customizes image acquisition parameters of the imaging device based at least in part upon the difference between the value corresponding to the physical characteristic as of the time of the prior study and the pre-determined threshold value.

35. The method of claim 27, wherein the medical imaging system automatically modifies at least one operating parameter of the radiation emitter of the imaging device without input by a user of the imaging device.

36. The method of claim 27, further comprising the medical imaging system, by the image acquisition workstation, storing the image of the subject's breast tissue acquired in the prior study to a computer readable storage medium, wherein the image acquisition workstation reads or retrieves the stored image from the computer readable storage medium for analysis of the pre-determined threshold value and determining whether one or more new images of the subject's breast tissue should be acquired.

* * * * *